United States Patent [19]

Siposs et al.

[11] 4,435,173
[45] Mar. 6, 1984

[54] VARIABLE RATE SYRINGE PUMP FOR INSULIN DELIVERY

[75] Inventors: George G. Siposs, Costa Mesa, Calif.; Jerry B. Christian, St. Louis, Mo.

[73] Assignee: Delta Medical Industries, Costa Mesa, Calif.

[21] Appl. No.: 355,102

[22] Filed: Mar. 5, 1982

[51] Int. Cl.³ .............................................. A61M 5/20
[52] U.S. Cl. ................................ 609/155; 128/DIG. 1
[58] Field of Search ................... 604/155, 152, 50, 65, 604/67, 245, 651; 122/DIG. 1, DIG. 12

[56] References Cited

U.S. PATENT DOCUMENTS

| | | | |
|---|---|---|---|
| 3,701,345 | 10/1972 | Heilman et al. | 604/155 X |
| 3,812,843 | 5/1974 | Wootten et al. | 604/155 X |
| 3,858,581 | 1/1975 | Kamen | 604/155 |
| 4,269,185 | 5/1981 | Whitney et al. | 604/155 |
| 4,278,085 | 7/1981 | Shim | 128/DIG. 12 |

Primary Examiner—Stephen C. Pellegrino
Attorney, Agent, or Firm—Allen A. Dicke, Jr.

[57] ABSTRACT

Variable rate pump for insulin delivery has as its pumping unit a syringe. A motor is connected to advance the syringe and electric signal pulses are produced during syringe advance. A control system permits selection of the interval between command pulses to maintain the desired base insulin delivery rate. A separate circuit drives the motor and syringe to deliver a predetermined bolus of insulin. Alarm circuits are connected to monitor the various system requirements and signal when they are not fulfilled.

12 Claims, 3 Drawing Figures

VARIABLE RATE SYRINGE PUMP FOR INSULIN DELIVERY

BACKGROUND OF THE INVENTION

This invention is directed to a selectable rate syringe pump for the delivery of insulin or other similar medication, including selection of the interval between motor-driven syringe advance and including control of the plunger displacement for delivery of an insulin bolus of predetermined size.

This pump is in the field of slow-rate, highly accurate dispensing pumps which can be used to inject small amounts of medication at a relatively constant rate for days at a time. This pump is sufficiently small that it can be carried on the patient's body. Such pumps have been found to be useful in treating certain diseases, such as cancer, where a slow, continuous infusion of medication seems to produce good results.

Another medical field of use is in the treatment of diabetes where a slow suitable rate of insulin dispensing provides for the patient's basal physiological requirements. A constant flow of insulin can be substituted by small, discrete amounts of medication at periodic intervals. Since the medication is subcutaneously administered, the diffusion of medication through the tissues provides a substantially steady supply to the physiological system. The regular dispensing of small amounts at relatively short periodic intervals does not appreciably differ from a constant rate injection.

In the field of diabetes, it has been found that most patients need approximately 0.014 unit of insulin per hour per kilogram of body weight. In addition, the patient needs an additional amount or "bolus" for each meal so that the food ingested can be properly metabolized. The amount of insulin in such a bolus usually depends on the amount and type of food to be eaten and the patient's own metabolic requirements. It is, therefore, desirable to have a pump which dispenses insulin at a substantially continuous rate and to have an additional capability for dispensing a bolus of predetermined size at a selected time.

The variable rate syringe pump of this invention is, in its preferred embodiment, particularly arranged for the delivery of insulin, and the invention is described as an insulin delivery system throughout this specification. However, it is clear that it is useful for the delivery of other medications to the body. For example, Heparin can be usefully delivered by this system. Furthermore, chemotherapy medication can be administered and controlled by the variable rate syringe pump of this invention. Thus, any medication which is desirably delivered to the patient over a prolonged period can be properly administered by the variable rate syringe pump of this invention. Liquid nourishment (hyperalimentation) can also be delivered.

Physicians have found that, when insulin is delivered to the body of the patient in very small doses regularly around the clock, the medical effect is better than if the medication is injected in infrequent large doses, such as by manual injection which is the orthodox method by which diabetics take insulin. As a result, a number of devices have been designed which are intended to administer medication at a "constant" rate. Injection systems in the prior art include M. Frey, et al., U.S. Pat. No. 3,395,704 which teaches a simple motor-operated syringe. D. Whitney, et al., U.S. Pat. Nos. 4,269,185 and 4,273,122 teach motor-operated syringes wherein the delivery rate is selected. W. Jewett, U.S. Pat. No. 3,415,419 has a rate selection system for the drive of a motor which actuates a syringe or a roller pump. A. Ruegg, U.S. Pat. No. 4,157,716 describes a syringe which is power-driven and in which the drive is stopped when a predetermined volume of medication has been dispensed. Such constant rate or constant volume delivery devices are useful in various medication-dispensing applications. However, when employed with the delivery of insulin, some of them require the dilution of standard insulin medication. Furthermore, in the treatment of diabetes, it is desirable to have a "base" rate dispensing which is related to the patient's general metabolism and to also have provision for the dispensing of a bolus of predetermined medication volume, on demand, such as at mealtimes.

Other pumps of the syringe type usually have one base rate of delivery or a very narrow range. The basal requirements are met by diluting the standard 100 units/cubic centimeter insulin medication so that, at the rate of delivery of the particular pump, the patient will receive the proper number of insulin units per hour, in accordance with his physiological demand. Dilution of the insulin is tedious and is subject to error. Dilution is required in these systems because the base rate of the pump is difficult to change after the pump is filled with the diluted insulin. The Mill-Hill pump is available from Harvard Apparatus, So. Natick, Mass. and is of a type where a bolus can be delivered by manually turning a knob to advance the plunger of the syringe. The advance of the plunger dispenses the insulin, but such an advance is cumbersome and prone to mistakes. Furthermore, it is not preselectable as to size. The Auto-Syringe pump produced in Hooksett, N.H., delivers a bolus upon operator command. The operator presses a fast-rate delivery switch and delivery continues until the operator releases the fast-rate delivery switch. He can observe delivery by way of a display unit which shows the number of units which have been delivered. This requires the operator's full attention and full time during the bolus delivery. In addition, this pump requires insulin dilution for base rate medication control.

The system described in George G. Siposs U.S. Pat. No. 4,398,908 for "Insulin Delivery System," Ser. No. 210,780. filed Nov. 28, 1980, provides for U-100 insulin being used, variable base rates and preselectable bolus size but the bi-valve reciprocating pump system is prone to air-lock between the valves.

SUMMARY OF THE INVENTION

In order to aid in the understanding of this invention, it can be stated in essentially summary form that it is directed to a variable rate syringe pump for insulin delivery wherein the interval between demand pulses is selected and a motor drives the syringe pump one increment to dispense a predetermined amount of medication for each demand pulse. A control system permits preselection of the demand pulse interval and a bolus control system permits preselection of a number of demand pulses and delivery of those demand pulses at will so that the syringe dispenses a predetermined bolus on demand. In addition, the control system includes circuitry which signals when the delivery system will soon be unable to continue the delivery and when it has not been able to deliver, as required.

It is, thus, an object of this invention to provide a delivery system which is particularly useful for the delivery of insulin and other similar medications wherein a preselected constant medication delivery rate is desired, with the delivery rate being supplemented by delivery on demand of additional medication.

It is another object to provide an insulin delivery system which includes a variable rate syringe pump which provides a slow, base-rate delivery of insulin as required by the basal metabolic requirement, and a preselected high rate on-demand preprandial delivery.

It is a further object to provide an insulin delivery system wherein an insulin delivery rate is preselected and the system is equipped with alarms which signal one or more conditions which may interfere with continued delivery of insulin at that rate, and may contain an indication that the desired insulin flow has not been achieved.

It is another object of this invention to provide a light, simple, portable liquid medication pumping system that combines all desired attributes of portable pump which can be connected to a hypodermic subcutaneous needle or cannula inserted into a vein, intestine or body cavity to dispense medication such as insulin, Heparin, chemotherapy medication, and the like to the patient's body at precisely the predetermined intervals at predetermined wide ranges of dosage rates, around the clock, with suitable alarms in association therewith so that improper delivery will be signaled.

It is a further object to provide a variable rate of insulin delivery system which includes a syringe pump which has connected thereto a flaccid reservoir so that, upon withdrawal of the syringe plunger, the syringe is refilled from the reservoir, to reduce the refill procedures.

Other objects and advantages of this invention will become apparent from a study of the following portion of this specification, the claims and the attached drawings.

DESCRIPTION OF THE PREFERRED EMBODIMENT

Figure 1:
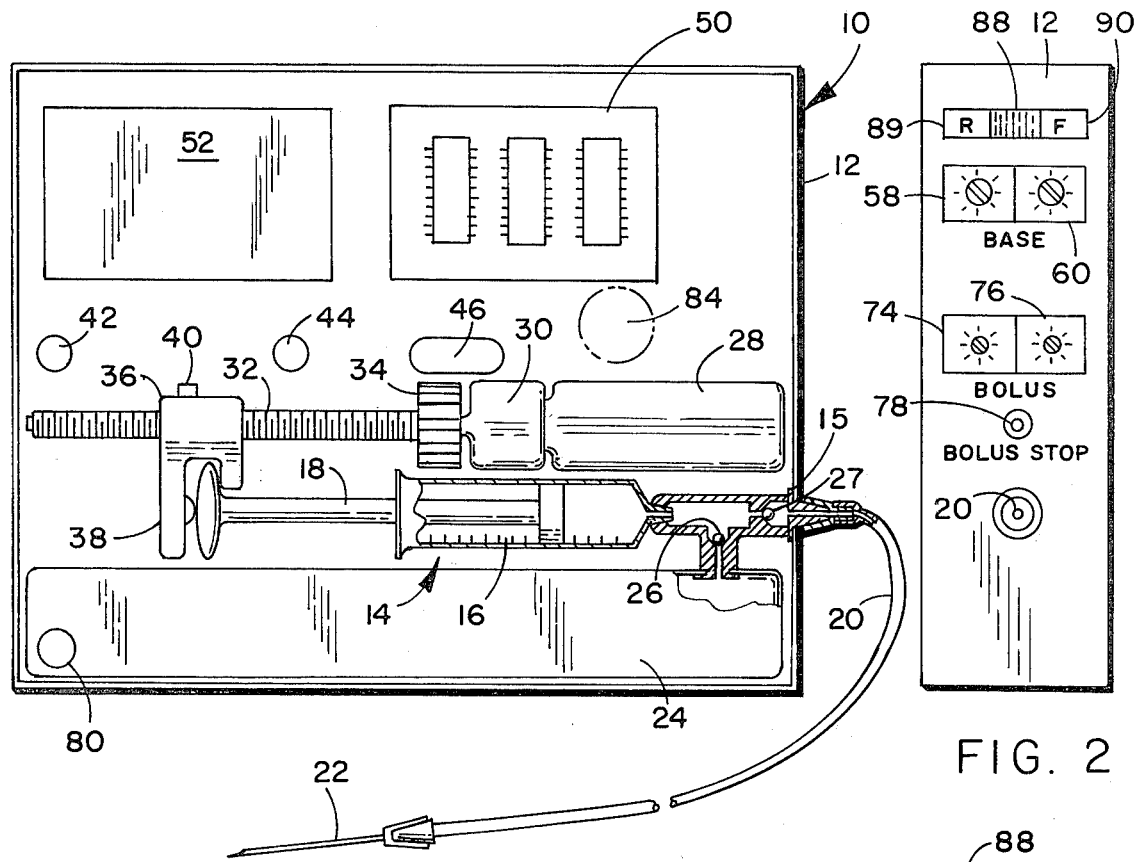
FIG. 1 is a plan view of the variable rate syringe pump of this invention, with its controls in a portable housing.

The variable rate syringe pump of this invention is generally indicated at 10 in FIG. 1. The pump 10 is a system particularly useful for the pumping of insulin at a preselected rate, with an insulin bolus of preselected size delivered at a selected time. It is a system, including a supply of medication for dispensement, a pump for dispensing the supply, a control system for the pump, preferably an alarm system to indicate when the delivery system is not fully responsive, and optionally, a supplemental reservoir from which the pump can be replenished. Housing 12 carries the components of the system, except for the subcutaneous needle and its tube. Housing 12 and its contents is sufficiently small that it is conveniently carried and can be worn by the person being supplied the insulin.

The device actually delivering the insulin as required is syringe 14 which has barrel 16 and plunger 18. Syringe 14 is illustrative of the preferred structure. However, while a literal syringe may not be used, a similar piston-cylinder combination may also be used. Furthermore, the seal in such a piston-cylinder combination may be a rolling diaphragm such as a "Bellofram." These structures can be conveniently described as piston pumps. The output connection 15 of syringe 14 is connected to medication tube 20 which carries hollow needle 22 on its outlet end. When the medication to be administered is insulin, needle 22 is subcutaneously inserted and may be taped in place. The outlet of syringe 14 can be directly connected to medication tube 20. However, when the optional medication reservoir 24 is employed, the reservoir 24 is connected to syringe 14 at its outlet. In the preferred embodiment illustrated, two check valves 26 and 27 are provided. Valve 26 is in communication with reservoir 24 and valve 27 is in communication with the outlet connection 15 of syringe barrel 16. When medication is being delivered, valve 27 permits it to pass out connector 15 and valve 26 prevents it from returning to The manner in which the reservoir and valve are active in the system will be described later.

Electric motor 28 has its output connected to a high ratio gear train in gear box 30 which has its output connected to rotate lead screw 32. Starwheel 34 rotates with the lead screw. Nut 36 is engaged on the threads of lead screw 32 and is rotationally restrained so that the nut moves axially of the lead screw when the lead screw rotates. Nut 36 carries arm 38 thereon which is positioned to engage on plunger 18 to drive the plunger into the syringe barrel to dispense medication. The amount of medication administered is a function of the pitch of the lead screw, the number of turns it makes, and syringe diameter. While motor 28 is shown as a standard rotary motor with a high-ratio gear train, instead it may be a solenoid and ratchet or a stepper motor mechanism. Thus, the electric motor 28 is the preferred embodiment of the general structure of an electrically powered driver.

Nut 36 carries magnet 40 which can actuate limit switches 42 or 44 when the nut 36 almost reaches the limits of its travel. In the inward direction of travel of nut 36, to the right in FIG. 1, limit switch 44 senses when the supply of insulin is nearly exhausted and emits a suitable signal. It also acts as a switch which stops further actuation of motor 28, beyond the end of stroke of the nut 36 and plunger 18.

Switch 46 is a similar device and is magnetically actuated by magnets mounted on starwheel 34. Pulse switch 46 emits a pulse each time a magnet on the starwheel passes it, to indicate rotation of the lead screw. Electric switches 42, 44 and 46 can be of the type commonly known as reed switches which are fully sealed and magnetically operated.

Figure 3:
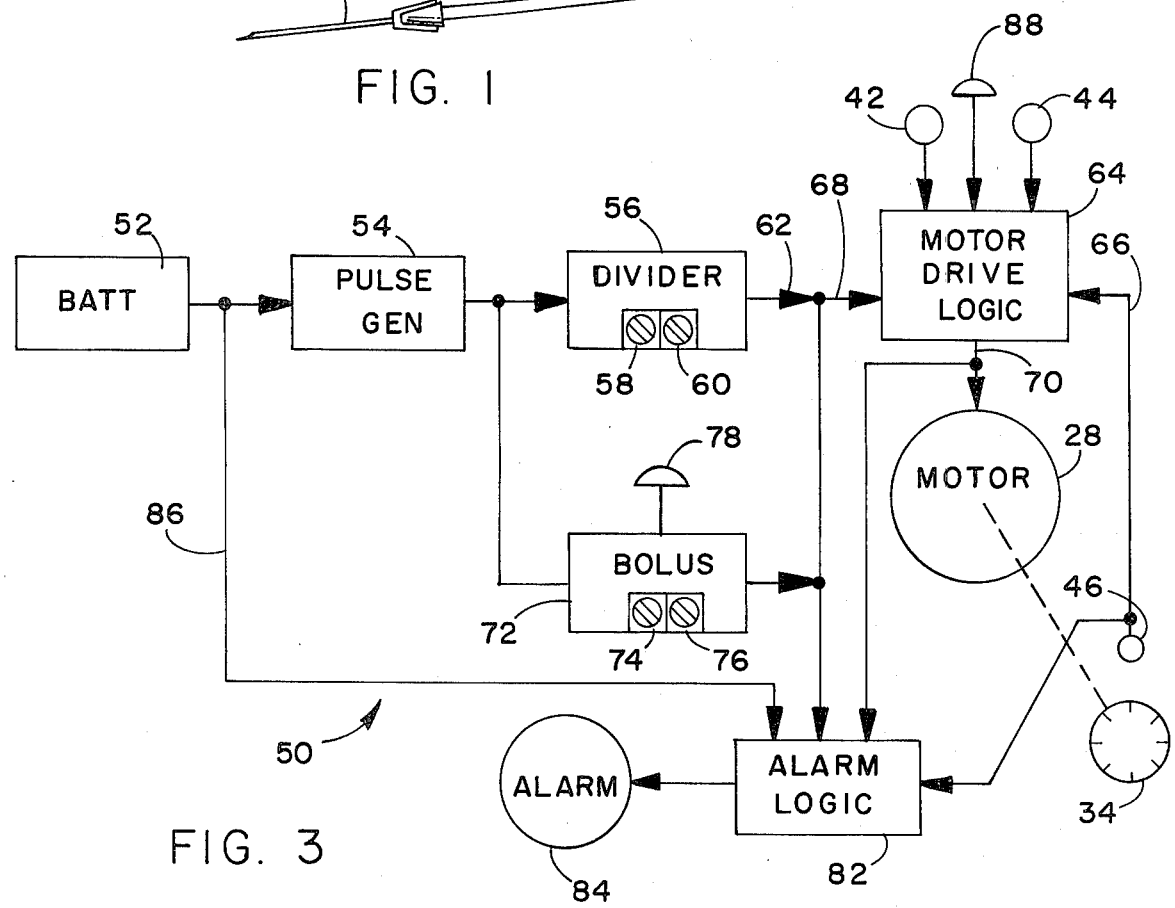
FIG. 3 is a block diagram of the control system for driving the syringe pump at its selected base rate delivery and its high rate on-demand preprandial delivery, together with the alarm logic.

FIG. 3 schematically illustrates control and alarm system 50 which drives the syringe pump in the desired manner and provides alarm signaling when an emergency condition exists. In order to maintain portability of the system, it is battery-powered as by battery 52. Battery 52 drives pulse generator 54 which emits pulses at the rate desired for bolus delivery, for example, one every minute. The output pulses of pulse generator 54 are delivered to base rate divider 56. Base rate divider 56 has manual selector knobs 58 and 60 by which the base rate period is determined. The base delivery rate of insulin is established by the period between pulses on base rate signal line 62. The base rate signals are delivered to motor drive logic 64 which is basically a pulse counter which receives base rate signal pulses from line 62 and also receives lead screw signal pulses from pulse switch 46 through signal line 66. As long as the command count in command line 68 is greater than the pulses signaled in line 66, motor 28 is driven in the forward direction. When the signal line 66 produces an equal number of counts, then motor drive logic 64 cuts off power to motor power line 70 and motor 28 is stopped.

Switch position 90 starts forward movement of the motor in accordance with the selector switch 58 and 60 settings. In the center position, switch 88 stops the battery current from reaching motor 28. The pump can be arranged to provide the best combination of delivery rates with readily available components. For example, when a Becton-Dickinson 3 cc syringe is used, its plunger travels 0.68 inch/cc. With a 64-turns-per inch lead screw and 6 magnets on the starwheel 34, each pulse will deliver approximately 0.38 unit of U-100 insulin. When 0.5 unit of insulin per hour is required as the base rate, the pump pulses will occur approximately at 45 minute intervals. For a base rate requirement of 1.0 unit per hour as base rate delivery, the base rate pulses in signal line 62 will occur at 23-minute intervals. Each pulse produces 1/6 turn of the lead screw.

The selector knobs 58 and 60 control divider 56 and control the interval between pulses. Knobs 58 and 60 are preferably calibrated so that higher numbers indicate higher base rate delivery. They may be directly calibrated in insulin units per hour or per day. In the preferred embodiment, two 10-position switches are used to select the base rate. This results in 100 possible choices. (Similarly, the bolus selector has 100 choices.)

As previously described, in addition to the base rate delivery of insulin for normal body metabolism, a preprandial insulin dosage is necessary at mealtimes. To enable this delivery, bolus counter 72 has an output to command line 68. Bolus counter 72 has manual selector knobs 74 and 76 which are manually preset in accordance with the desired size of the bolus. As previously indicated with respect to the specific example, each pump pulse delivers approximately 0.38 units of U-100 insulin. When the bolus size is established and 0.38 is divided thereinto, the result is the number of pulses required to deliver that bolus. These calculations are preferably already incorporated into the calibration of selector knobs 74 and 76 so that the amount of bolus can be set thereon in terms of insulin units. Bolus delivery does not commence until bolus start button 78 is pressed. The pulses from pulse generator 54 are transmitted through the bolus counter to command line 68. As previously described, these pulses cause the motor to be driven a proportionate amount. When the total number of pulses out of the bolus counter 72 reaches the selected bolus limit, the bolus counter shuts off its output.

FIG. 3 illustrates alarm logic 82 connected to the control system 50 in order to signal when the desired amount of insulin is not being delivered. Alarm logic circuit 82 has a visible and/or audible alarm 84 connected to be actuated thereby. Battery voltage line 86 is connected to logic 82 to indicate low battery voltage. As previously noted, low level limit switch 44 is connected to the alarm logic to signal the end of stroke.

Figure 2:
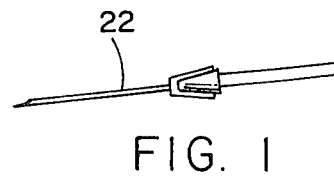
FIG. 2 is a end view of the pump housing of FIG. 1, showing the manual control knobs thereon.

Syringe 14 may be refilled by connecting the nozzle connector 15 of barrel 16 to an insulin supply and manually withdrawing plunger 18 (past arm 38). Also, alternatively, switch 88, see FIG. 2, can be moved into the reverse position, where the motor drives nut 36 to the outer limit switch 42 at which the motor stops. In this case, arm 38 is connected to plunger 18 so that medication can be drawn into syringe 14 by motorized means. Alternatively, a newly filled syringe can be inserted into the pump.

In order to permit refilling the syringe 14 without access to a separate supply of medication, reservoir 24 within housing 12 may carry that extra supply of medication. When the plunger is withdrawn, the medication is drawn through check valve 26 from the reservoir into the barrel. Thereafter, depression of the plunger would deliver the medication out of the nozzle 15 into tube 20 through valve 27. Reservoir 24 is flaccid so it does not apply pressure to the medication contained therein. There is a filler port 80 provided so that the reservoir may be filled at the factory or by the patient.

This invention has been described in its presently contemplated best mode, but it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A variable rate pump for insulin delivery comprising:
    a piston pump having an output for connection for delivery of medication to a patient, said piston pump having a piston therein;
    electrical motor drive means connected to said piston to move said piston in said pump to dispense medication from said pump, said electric motor means comprising a pulse-driven electric motor having an output shaft, said output shaft being connected to a lead screw, a nut on said lead screw to move axially of said lead screw when said lead screw rotates, said nut being in engagement with said plunger to move said plunger as said motor rotates, a wheel connected to rotate with said lead screw, a plurality of magnetic poles on said wheel, said motor drive means including a pulse switch, said pulse switch being a magnetically controlled switch mounted directly adjacent said wheel and controlled by said wheel to produce signal pulses as said motor moves said plunger;
    control means for controlling said motor, said control means having pulse interval selection means for producing a base command pulse rate which is proportional to the desired medication dispensing command rate, said pulse switch being connected to said motor control means so that the pulses produced as said motor moves said piston are counted by said control means and are compared to the command pulses delivered for controlling said motor, said base rate selection means being manually selectable, said control means also including a bolus control means connected to deliver a preselected number of bolus command pulses to said motor drive means for the delivery of a preselected amount of medication.

2. The variable rate pump of claim 1 wherein said wheel is directly mounted on said lead screw.

3. The variable rate pump of claim 1 wherein first and second limit switches are positioned adjacent said nut to signal when said nut approaches first and second limit positions along said lead screw.

4. The variable rate pump of claim 3 wherein said limit sensors are magnetically control switches and a magnetic pole is carried on said nut so that the approach of said nut to said first and second magnetic limit sensors actuates switches in said first and second limit sensors, said switches being connected to said control means for controlling said motor.

5. A variable rate pump for insulin delivery comprising:
- a housing, said housing being sufficiently small to be portable, a piston pump having a cylinder in said housing, said piston pump having an output connection for delivery of medication of medicine to a patient carrying said pump, a piston in said cylinder so that as said piston is moved into said cylinder, medication is dispensed from the output connection of said cylinder;
- a electric motor within said housing, a lead screw connected to be rotated by said electric motor, a nut on said lead screw, said nut being adjacent said piston for driving said piston into said cylinder so that as said motor rotates medication is dispensed to the patient carrying said pump;
- electrical control means within said housing for controlling said motor, said electrical control means including a battery, a pulse generator connected to be energized by said battery, selectable pulse divider means connected to said pulse generator for selectably dividing the pulses from said pulse generator so that a selectable base command pulse rate proportional to a desired base medication delivery rate is produced, said divider being connected to said motor so that said motor is driven in proportion to said base command pulse rate so that said piston advances within said cylinder and delivers medication at a base rate;
- a selectable counter connected to said pulse generator, said selectable counter being settable to pass a preselected number of bolus command pulses, said counter being connected to said motor so that when the count of bolus command pulses is delivered to said motor, said motor actuates said piston so that it dispenses the preselected bolus of medication, whereby said pump delivers medication at a preselected base rate and in addition on demand delivers a medication bolus of predetermined size.

6. The pump of claim 5 wherein a pulse switch is connected to said screw to generate control pulses as said screw rotates, said pulse generator being connected to said motor control means to control said motor with command pulses from said divider, with bolus command pulses from said counter and with control pulses from said pulse switch.

7. The pump of claim 5 wherein first and second limit sensors are positioned adjacent said nut, said first and second limit sensors being connected to said motor control means to limit motion of said nut as said nut approaches said first and second sensors.

8. The pump of claim 7 wherein said first and second limit sensors are magnetically controlled switches and a magnet is positioned on said nut to actuate said first and second sensors as said nut approaches said first and second sensors.

9. A variable rate pump for insulin delivery comprising:
- a housing, said housing being sufficiently small to be portable, a piston pump having a cylinder in said housing, said piston pump having an output connection for delivery of medication of medicine to a patient carrying said pump, a piston in said cylinder so that as said piston is moved into said cylinder, medication is dispensed from the output connection of said cylinder;
- a electric motor within said housing, a lead screw connected to be rotated by said electric motor, a nut on said lead screw, said nut being adjacent said piston for driving said piston into said cylinder so that as said motor rotates medication is dispensed to the patient carrying said pump;
- electrical control means within said housing for controlling said motor, said electrical control means including a battery, a pulse generator connected to be energized by said battery, selectable pulse divider means connected to said pulse generator for selectably dividing the pulses from said pulse generator so that a selectable base command pulse rate proportional to a desired base medication delivery rate is produced, said divider being connected to said motor so that said motor is driven in proportion to said base command pulse rate so that said piston advances within said cylinder and delivers medication at a base rate;
- a selectable counter connected to said pulse generator, said selectable counter being settable to pass a preselected number of bolus command pulses, said counter being connected to said motor so that when the count of bolus command pulses is delivered to said motor, said motor actuates said piston so that it dispenses the preselected bolus of medication, whereby said pump delivers medication at a preselected base rate and in addition on demand delivers a medication bolus of predetermined size;
- a soft, collapsible, non-vented reservoir within said housing, valve means connecting said reservoir with said output connection of said barrel so that said reservoir feeds said cylinder when said piston is withdrawn and said cylinder feeds said outlet connection when said piston is depressed.

10. The pump of claim 9 wherein said valves means between said reservoir and said outlet connection are check valves.

11. The pump of claim 9 further including filler plug means on said reservoir so that even if said pump is implanted, said reservoir can be refilled transcutaneously via a needle.

12. A variable rate pump for insulin delivery comprising:
- a housing;
- a syringe having a barrel and having a plunger with said plunger being movable into said barrel on an axis, said barrel having an outlet on the end thereof opposite said plunger;
- plunger drive means within said housing, said plunger drive means being for driving said plunger and comprising a lead screw lying parallel to said axis of said barrel, a nut on said lead screw, said nut being engaged with said plunger so that upon rotation of said lead screw in a first direction said plunger is moved into said barrel and upon rotation of said lead screw in a second direction said plunger is withdrawn from said barrel;
- motor means connected to rotate said lead screw a selected amount for moving said plunger within its barrel by a selected amount;
- a soft, flaccid, collapsible, non-vented reservoir within said housing, valve means connecting said reservoir with said outlet from said barrel so that said reservoir feeds said barrel when said plunger is withdrawn and said barrel feeds said outlet connection when said plunger is depressed, said outlet connection including connection means by which said outlet delivers insulin to a patient for patient medication.

* * * * *